US007741480B2

(12) United States Patent
Rao et al.

(10) Patent No.: US 7,741,480 B2
(45) Date of Patent: *Jun. 22, 2010

(54) PROCESS FOR THE PREPARATION OF LINEZOLID AND RELATED COMPOUNDS

(75) Inventors: Dodda Mohan Rao, Hyderabad (IN); Pingili Krishna Reddy, Hyderabad (IN)

(73) Assignee: Symed Labs Limited, Hyderabad (IN)

( * ) Notice: Subject to any disclaimer, the term of this patent is extended or adjusted under 35 U.S.C. 154(b) by 30 days.

This patent is subject to a terminal disclaimer.

(21) Appl. No.: 11/868,633

(22) Filed: Oct. 8, 2007

(65) Prior Publication Data

US 2008/0021215 A1 Jan. 24, 2008

Related U.S. Application Data

(62) Division of application No. 10/524,746, filed as application No. PCT/IN2004/000105 on Apr. 19, 2004, now Pat. No. 7,307,163.

(51) Int. Cl.
C07D 413/10 (2006.01)
(52) U.S. Cl. ..................................... 544/137
(58) Field of Classification Search .................. 544/137
See application file for complete search history.

(56) References Cited

U.S. PATENT DOCUMENTS

| 5,688,792 | A | 11/1997 | Barbachyn et al. |
| 5,837,870 | A | 11/1998 | Pearlman et al. |
| 6,444,813 | B2 | 9/2002 | Bergren |
| 6,559,305 | B1 | 5/2003 | Bergren |
| 6,750,341 | B2 | 6/2004 | Krochmal et al. |
| 7,307,163 | B2 | 12/2007 | Rao |
| 7,351,824 | B2 | 4/2008 | Rao et al. |
| 7,429,661 | B2 | 9/2008 | Rao et al. |
| 7,524,954 | B2 * | 4/2009 | Rao et al. .................. 544/137 |
| 2002/0095054 | A1 | 7/2002 | Pearlman |
| 2004/0102523 | A1 | 5/2004 | Broquaire et al. |
| 2006/0142283 | A1 | 6/2006 | Aronhime et al. |
| 2006/0247435 | A1 | 11/2006 | Rao |
| 2008/0021215 | A1 | 1/2008 | Rao et al. |

FOREIGN PATENT DOCUMENTS

| CN | 1355165 | 6/2002 |
| EP | 004024 | 2/1979 |
| EP | 50827 | 10/1981 |
| EP | 0275742 | 12/1987 |
| EP | 1255754 | 6/2005 |
| FR | 2506769 | 6/1978 |
| WO | 9507271 A1 | 8/1994 |
| WO | 9737980 | 12/1997 |
| WO | WO 9737980 | 12/1997 |
| WO | 9924393 A1 | 10/1998 |
| WO | 0170170 | 9/2001 |
| WO | WO 0170170 | 9/2001 |
| WO | 02085849 | 10/2002 |
| WO | WO 02085849 | 10/2002 |
| WO | 2005099353 A2 | 4/2004 |
| WO | 2005099353 A3 | 10/2005 |

OTHER PUBLICATIONS

K.V.S.R. Krishna Reddy, S. Mahender Rao, G. Om Reddy, T. Suresh, J. Moses Babu, P.K.Dubey, K. Vyas, Isolation and Characterization of Process-Related Impurities in Linezolid, Journal of Pharmaceutical and biomedical Analysis 30 (2002) 635-642.
Braj B. Lohray, Sundarababu Baskaran, B. Srinivasa Rao, B. Yadi Reddy and I. Nageswara Rao, A Short Synthesis of Oxazolidinone Derivatives Linezolid and Eperezolid: A New Class of Antibacterials, Tetrahedron Letters 40 (1989) 4855-4856.
Steven J. Brickner, et al., Synthesis and Antibactreial Activity of U-100592 and U-100766, Two Oxazolidinone Antibacterial Agents for the Potential Treatment of Multidrug-Resistant Gram-Positive Bacterial Infections, J. Med chem 1996, 39, 673-679.
U.S. Appl. No. 10/524,478, filed Feb. 11, 2005.
U.S. Appl. No. 11/861,340, filed Sep. 26, 2007.
U.S. Appl. No. 11/861,406, filed Sep. 26, 2007.
U.S. Appl. No. 11/861,433, filed Sep. 26, 2007.
U.S. Appl. No. 11/868,662, filed Oct. 8, 2007.
Bernstein "Polymorphism in Molecular Crystals", p. 117-118, 272 (2002).
Davidovich et al. "Detection of polymorphism by Powder X-Ray Diffraction: Interference by Preferred Orientation", Am. Pharm. Rev., vol. 7(1), p. 10, 12, 14, 16, 100 (2004).
US Pharmacopia, #23 National Formulary #18, p. 1843-1844 (1995).
Banga S. Chawla G. Bansal AK, New trends in crystallization of active pharmaceutical ingredients, Business Briefing: Pharmagenerics 2004, Nov. 1-5.

(Continued)

Primary Examiner—Rebecca L Anderson
(74) Attorney, Agent, or Firm—Caesar, Rivise, Bernstein, Cohen & Pokotilow, Ltd.

(57) ABSTRACT

The present invention provides a novel process for preparation of 5-aminomethyl substituted oxazolidinones, key intermediates for oxazolidinone antibacterials including linezolid. Thus linezolid is prepared by a) reacting 3-fluoro-4-morpholinyl aniline with R-epichlorohydrin;
b) subjecting N-[3-Chloro-2-(R)-hydroxypropyl]-3-fluoro-4-morpholinyl aniline produced above to carbonylation;
c) reacting (5R)-5-(chloromethyl)-3-[3-fluoro-4-(4-morpholinyl)phenyl]-2-oxazolidinone produced above with potassium phthalimide;
d) reacting (S)-N-[[3-[3-Fluoro-4-[4-morpholinyl]phenyl]-2-oxo-5-oxazolidinyl]methyl]phthalimide produced above with hydrazine hydrate; and
e) reacting S-N-[[3-[3-Fluoro-4-[4-morpholinyl]phenyl]-2-oxo-5-oxazolidinyl]methyl]amine produced above with acetic anhydride to produce linezolid.

6 Claims, No Drawings

OTHER PUBLICATIONS

The United States Pharmacopoeia, 23rd Edition, National Formulary #18, U.S. Pharmacopoeia Convention, Inc., Rockville, MD, 1995, pp. 1843-1844.

European and Japanese Pharmacopoeias as part of the International Harmonization Procedure (Pharmeuropa, vol. 14, No. 1, Jan. 2002, p. 185-191).

International Search Report dated Oct. 16, 2003.

Chawla et al. Challenges in Polymorphism of Pharmaceuticals, CRIPS, vol. 5, No. 1, Jan.-Mar. 2004.

Newman et al., Solid-state analysis of the active pharmaceutical ingredient in drug products, DDT, vol. 8, No. 19, Oct. 2003, pp. 898-905.

Bernstein "Polymorphism in Molecular crystals" p. 117-118, 272(2002).

U.S. Appl. No. 11/868,633, filed Oct. 8, 2007.

Chawla et al. Challenges in Polymorphism of Pharmaceuticals, CRIPS vol. 5, No. 1, Jan.-Mar. 2004.

Banga S. Chawla G. Bansal AK. New trends in crystallization of active pharmaceutical ingredients, Business Briefing: Pharmagenerics 2004, Nov. 1-5.

* cited by examiner

PROCESS FOR THE PREPARATION OF LINEZOLID AND RELATED COMPOUNDS

This application is a Divisional of 10/524,746, filed Feb. 15, 2005, now U.S. Pat. No. 7,307,163, which is a National Stage Entry of PCT/IN04/00105, filed Apr. 19, 2004.

FIELD OF THE INVENTION

The present invention provides a novel process for preparation of 5-aminomethyl substituted oxazolidinones, key intermediates for oxazolidinone antibacterials.

BACKGROUND OF THE INVENTION

U.S. Pat. No. 5,688,792 (U.S. Pat. No. 5,688,792) disclosed oxazine and thiazine oxazolidinone derivatives. The compounds are antimicrobial agents. Among them linezolid, chemically N-[[(5S)-3-[3-fluoro-4-(4-morpholinyl)phenyl]-2-oxo-5-oxazolidinyl]methyl]acetamide is the most important antibacterial agent. Linezolid is represented by the following structure:

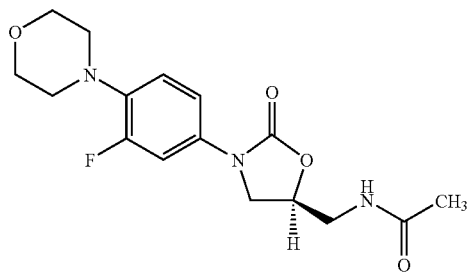

Processes for preparation of linezolid were described in U.S. Pat. No. 5,837,870, WO 99/24393, WO 95/07271, J. Med. Chem. 39(3), 673-679, 1996 and Tetrahedron Lett., 40(26), 4855, 1999.

According to prior art processes, the 5-hydroxymethyl substituted oxazolidinones are converted to the corresponding 5-aminomethyl substituted oxazolidinones, key intermediates in the production of oxazolidinone antibacterial pharmaceuticals.

The prior art processes for preparing 5-aminomethyl substituted oxazolidinones are associated with many drawbacks. For instant in the preparation of linezolid, WO 95/07271 uses butyl lithium at very low temperature (−78° C.) and WO 99/24393 uses phosgene gas. It is known that the handling of butyl lithium and phosgene gas are difficult and the person skilled in the art appreciate a process that produces the product in good yield avoiding the 'difficult to handle' reagents.

We have discovered a novel process for preparation of 5-aminomethyl substituted oxazolidinone key intermediates using novel intermediates. The novel process solve the drawbacks associated with the prior processes and so, commercially viable for preparing these and related compounds.

SUMMARY OF INVENTION

The present invention provides a novel process to prepare 5-aminomethyl substituted oxazolidinones of formula I:

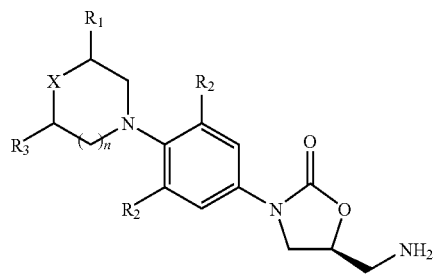

wherein
  X is O, S, SO or $SO_2$;
  $R_1$ is H, $CH_3$ or CN;
  $R_2$ is independently H, F or Cl;
  $R_3$ is H or $CH_3$;
  n is 0, 1 or 2;

which comprises;
a) reacting a compound of formula II:

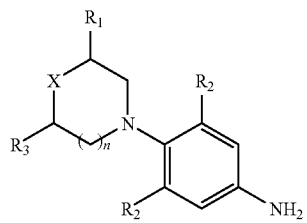

wherein $R_1$, $R_3$, X, $R_2$ and n are as defined in formula I; with R-epichlorohydrin of formula III:

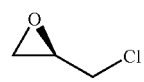

to produce a compound of formula IV:

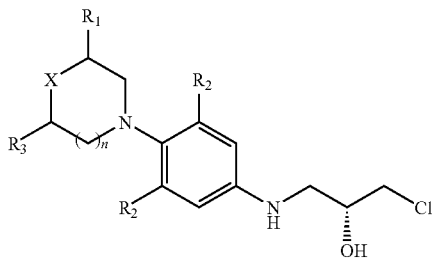

wherein $R_1$, $R_3$, X, $R_2$ and n are as defined in formula I;

b) converting the product of step (a) to chloromethyl oxazolidinone compound of formula V:

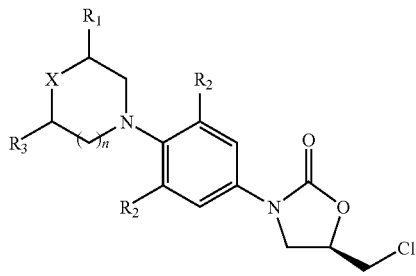

wherein $R_1$, $R_3$, X, $R_2$ and n are as defined in formula I; and c) converting the chloromethyl oxazolidinone compound of step (b) to aminomethyl oxazolidinone of formula I.

The compounds of formula IV are novel and provides another aspect of the present invention.

The compounds of the formula V with the exception of the compound of formula V wherein $R_1=R_3$ is H; one $R_2$ is H and the other $R_2$ is F; X is O; and n is 1 are novel.

DETAILED DESCRIPTION OF THE INVENTION

The present invention provides a novel process for preparing 5-aminomethyl substituted oxazolidinones of formula I:

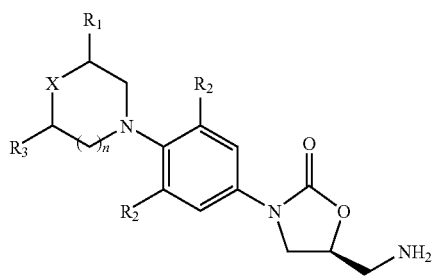

wherein
X is O, S, SO or $SO_2$;
$R_1$ is H, $CH_3$ or CN;
$R_2$ is independently H, F or Cl;
$R_3$ is H or $CH_3$;
n is 0, 1 or 2.

Step—a) Phenyl amine compound of formula II:

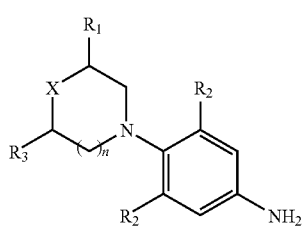

wherein $R_1$, $R_3$, X, $R_2$ and n are as defined in formula I;

is reacted with R-epichlorohydrin of formula III:

to provide chlorohydrin compound of formula IV:

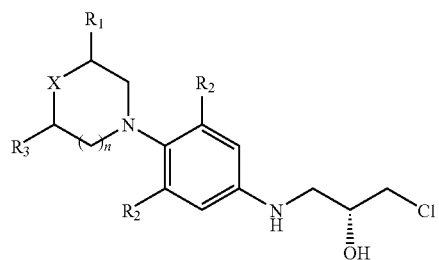

wherein $R_1$, $R_3$, X, $R_2$ and n are as defined in formula I.

The quantity of epichlorohydrin is not critical, but for better yield at least one molar equivalent is required per equivalent of phenyl amine of formula II.

The reaction may be carried out with or without using a solvent.

If the reaction is carried out in the absence of solvent, the compounds of formula II and the formula III are usually heated together for sufficient time to obtain the compound of formula IV. The reactants are heated preferably to about 40-150° C. and more preferably to about 40-120° C. The time required for the conversion is 30 minutes to 10 hours, preferably 2 to 6 hours.

Preferably, the reaction between the compounds of formula II and formula III is carried out in a solvent. Any solvent, which is neutral towards the reactants, may be used. Operable solvents include cyclic ethers such as tetrahydrofuran; amides such as N,N-dimethylformamide and N,N-dimethylacetamide; acetonitrile; and alcohols such as methanol, ethanol, t-amyl alcohol, t-butyl alcohol and Isopropyl alcohol; and a mixture thereof. Preferable solvent is selected from methanol, isopropyl alcohol and N,N-dimethylformamide.

The reaction is performed at or below boiling temperature of the solvent used, more preferably between 10° C. and boiling temperature of the solvent used and even more preferably at boiling temperature of the solvent used.

Time required for completion of the reaction depends on factors such as solvent used and temperature at which the reaction is carried.

The product obtained may be used directly in the next step, or it can be isolated from the reaction mixture and used in the next step.

The compounds of formula IV are novel and provides another aspect of the present invention.

Step—b) The chlorohydrin compound of formula IV produced as above is subjected to carbonylation to provide chloromethyl oxazolidinone compound of formula V:

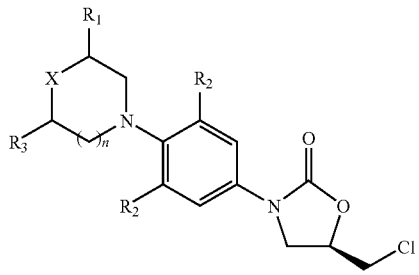

wherein $R_1$, $R_3$, X, $R_2$ and n are as defined in formula I.

The carbonylation is performed using any carbonylating reagent commonly known for such purpose. Among them carbonyldiimidazole, phosgene, methyl chloroformate, benzyl chloroformate and phenylchloroformate are preferred; carbonyldiimidazole being more preferred.

The carbonylation reaction is preferably performed by contacting the chlorohydrin compound of formula IV with carbonylating agent in the presence of an aprotic solvent or a mixture thereof. More preferably the chlorohydrin compound of formula IV is reacted with at least one molar equivalent of the carbonylating agent in the presence of an aprotic solvent such as methylene dichloride, ethylenedichloride or chloroform.

The compound of formula V wherein $R_1=R_3$ is H; X is O; one $R_2$ is H and the other $R_2$ is F; n is 1 ((5R)-5-(chloromethyl)-3-[3-fluoro-4-(4-morpholinyl)phenyl]-2-oxazolidinone) is mentioned in the J. Pharmaceutical and biomedical analysis, 2002, 30 (3), 635-642 as an possible impurity in linezolid. We disclosed the use of this compound and related compounds in the preparation of the compounds of formula I.

The compounds of formula V, wherein X, $R_1$, $R_2$, $R_3$ and n are as defined in formula I with the exception of the compound of formula V, wherein $R_1=R_3$ is H; one $R_2$ is H and the other $R_2$ is F; X is O; and n is 1 are novel and provide another aspect of present invention.

Step—c) The chloromethyl oxazolidinone compound of formula V produced as above is converted to aminomethyl oxazolidinone compound of formula I.

Preferred 5-amino methyl substituted oxazolidinones are the compounds of formula 1, wherein $R_1=R_3$ is H; $R_2$ is independently H and F; X is O or S; and n is 1. More preferred 5-amino methyl substituted oxazolidinones are the compounds of formula 1, wherein $R_1=R_3$ is H; $R_2$ is independently H and F; X is O; and n is 1. Still more preferred 5-amino methyl substituted oxazolidinones are the compounds of formula 1, wherein $R_1=R_3$ is H; one $R_2$ is H and the other $R_2$ is F; X is O; and n is 1.

The conversion of the compound of formula V to the compound of formula I can be achieved by a method known for the conversion of aliphatic chloride to the corresponding amine.

Thus, for example, chlorine atom of the chloromethyl oxazolidinone compound is first replaced by azide using azide source such as sodium azide or potassium azide to provide azide compound of formula VI:

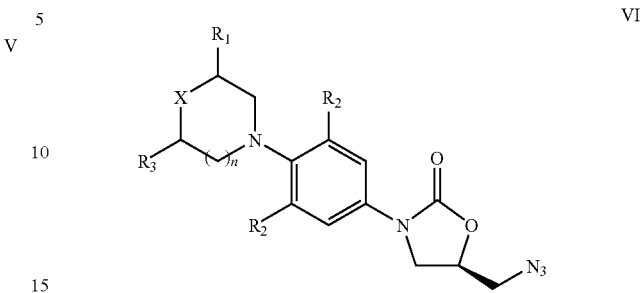

wherein $R_1$, $R_3$, X, $R_2$ and n are as defined in formula I.

The azide compound is known and can be converted to the aminomethyl oxazolidinone compound by known methods such as those described in U.S. Pat. No. 5,688,792. For example, the azide compound is hydrogenated using for example palladium/carbon catalyst to provide the aminomethyl oxazolidinone compound.

Alternatively, the chloromethyl oxazolidinone compound is reacted with potassium phthalimide to provide phthalimido compound of formula VII:

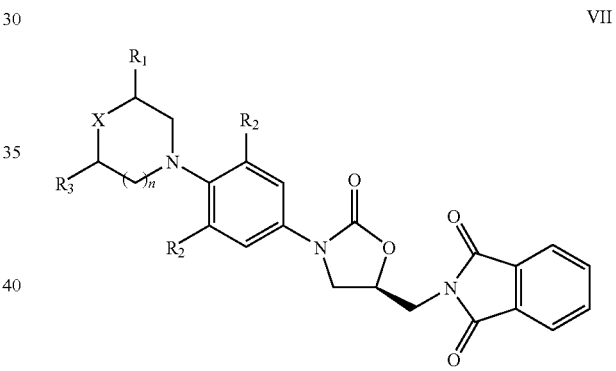

wherein $R_1$, $R_3$, X, $R_2$ and n are as defined in formula I.

The reaction is carried out by contacting the 5-chloromethyl oxazolidinones with potassium phthalimide in a solvent or mixture of solvents. Selection of solvent is not critical, but preferable solvents are those that dissolve both the chloromethyl oxazolidinones and potassium phthalimide to ensure maximum contact between the reactants resulting in faster reaction. However, the process is also operable with solvents that only partially dissolve the chloromethyl oxazolidinones or potassium phthalimide. The preferable solvent is dimethyl formamide or acetonitrile.

The reaction is performed preferably between about 10° C. and the boiling temperature of the solvent used, more preferably between 40° C. and 100° C. and most preferably at the boiling temperature of the solvent used.

Time required for completion of the reaction depends on factors such as solvent used and temperature at which the reaction is carried out. For example, if the reaction is carried out by contacting the 5-chloromethyl oxazolidinones with potassium phthalimide in dimethylformamide under reflux conditions, about 2 to 10 hours is required for the reaction completion.

The phthalimido compounds of formula are known and can be converted to the aminomethyl oxazolidinone compounds by using for example Hydrazine hydrate or aqueous methylamine. These methods are known and are described for example in U.S. Pat. No. 5,688,792.

The aminomethyl oxazolidinone compounds of formula I are acylated by known methods using acylating agents such as acyl halides or acyl anhydrides to form the corresponding 5-acylaminomethyloxazolidinone compounds of formula VIII.

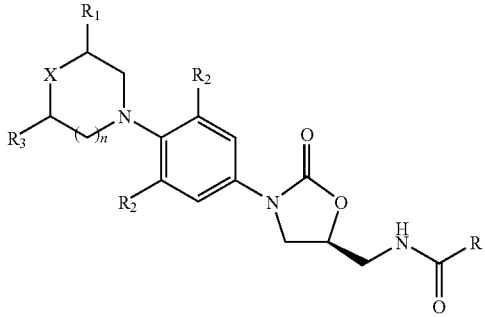

VIII wherein $R_1$, $R_3$, X, $R_2$ and n are as defined in formula I; R represents $C_1$ to $C_8$ straight or branched alkyl groups. The preferred alkyl group is $CH_3$.

The acylation can be carried out by known methods such as those described in U.S. Pat. No. 5,688,792.

One compound of formula Vil can be converted to another compound of formula VII. Thus for example compounds of formula VIII, wherein X is S can be converted to the compounds of formula VIII, wherein X is SO or $SO_2$ by the methods such as those disclosed in U.S. Pat. No. 5,688,792.

The 5-acyl amino methyl substituted oxazolidinone of formula VIII are known to be antibacterial pharmaceutical agents.

R-Epichlorohydrin has the right configuration to obtain the compounds of formula I and VIII. The configuration of epichlorohydrine is retained through out the sequence of reactions of the invention. However, it is readily apparent to one skilled in the art that one could easily perform the identical process steps with the opposite enantiomeric form or racemic form to obtain the corresponding stereo isomers.

Therefore, using the chemistry of the claimed process with any of the enantiomeric forms is considered equivalent to the claimed processes.

In particular most important compound of formula VIII is linezolid (VIII, $R_1$ and $R_3$ is H; X is O, one $R_2$ is H and the other $R_2$ is F; n is 1). The most preferred process for preparing linezolid is described as under:

a) 3-fluoro-4-morpholinyl aniline (formula II, $R_1=R_3$ is H; X is O; one $R_2$ is H and the other $R_2$ is F; and n is 1) is reacted with R-epichlorohydrin (formula III) to produce N-[3-Chloro-2-(R)-hydroxypropyl]-3-fluoro-4-morpholinyl aniline (formula IV, $R_1=R_3$ is H; X is O; one $R_2$ is H and the other $R_2$ is F; and n is 1);

The quantity of epichlorohydrin is not critical, but for better yield at least one molar equivalent is required per equivalent of 3-fluoro-4-morpholinyl aniline.

Any solvent, which is neutral towards the reactants, may be used. Operable solvents include cyclic ethers such as tetrahydrofuran; amides such as N,N-dimethylformamide and N,N-dimethylacetamide; acetonitrile; and alcohols such as methanol, ethanol, t-amyl alcohol, t-butyl alcohol and Isopropyl alcohol. Preferable solvent is selected from methanol, isopropyl alcohol and N,N-dimethylformamide.

The reaction is performed at or below boiling temperature of the solvent used, more preferably between 10° C. and boiling temperature of the solvent used and even more preferably at boiling temperature of the solvent used.

Time required for completion of the reaction depends on factors such as solvent used and temperature at which the reaction is carried. For example, if the reaction is carried out in isopropyl alcohol solvent at the boiling temperature of the solvent, about 15 hours is required for the reaction completion.

The product obtained can be used directly in the next step, or it can be isolated from the reaction mixture and used in the next step.

b) N-[3-Chloro-2-(R)-hydroxypropyl]-3-fluoro-4-morpholinyl aniline produced as above is subjected to carbonylation to provide (5R)-5-(chloromethyl)-3-[3-fluoro-4-(4-morpholinyl)phenyl]-2-oxazolidinone (Formula V, $R_1=R_3$ is H; X is O; one $R_2$ is H and the other $R_2$ is F; and n is 1).

The carbonylation is performed using any carbonylating reagent commonly known for such purpose. Among them carbonyldiimidazole, phosgene, methyl chloroformate, benzyl chloroformate and phenylchloroformate are preferred; carbonyldiimidazole being more preferred.

The carbonylation reaction is preferably performed by contacting the N-[3-Chloro-2-(R)-hydroxypropyl]-3-fluoro-4-morpholinyl aniline with carbonylating agent in the presence of an aprotic solvent or a mixture of aprotic solvents. More preferably the N-[3-Chloro-2-(R)-hydroxypropyl]-3-fluoro-4-morpholinyl aniline is reacted with at least one molar equivalent of the carbonylating agent in the presence of an aprotic solvent such as methylene dichloride, ethylenedichloride or chloroform.

c) (5R)-5-(chloromethyl)-3-[3-fluoro-4-(4-morpholinyl) phenyl]-2-oxazolidinone produced as above is reacted with potassium phthalimide to provide (S)-N-[[3-[3-Fluoro-4-[4-morpholinyl]phenyl]-2-oxo-5-oxazolidinyl] methyl]phthalimide (Formula VII, $R_1=R_3$ is H; X is O; one $R_2$ is H and the other $R_2$ is F; and n is 1);

The reaction is carried out by contacting the (5R)-5-(chloromethyl)-3-[3-fluoro-4-(4-morpholinyl)phenyl]-2-oxazolidinone with potassium phthalimide in a solvent or a mixture of solvents. Selection of solvent is not critical, but preferable solvents are those that dissolve both the chloromethyl oxazolidinones and potassium phthalimide to ensure maximum contact between the reactants resulting in faster reaction. However, the process is also operable with solvents that only partially dissolve the chloromethyl oxazolidinones or potassium phthalimide. The preferable solvent is dimethyl formamide or acetonitrile.

The reaction is performed preferably between about 10° C. and the boiling temperature of the solvent used, more preferably between 40° C. and 100° C. and most preferably at the boiling temperature of the solvent used.

Time required for completion of the reaction depends on factors such as solvent used and temperature at which the reaction is carried out. For example, if the reaction is carried out by contacting the 5-chloromethyl oxazolidinones with potassium phthalimide in dimethylformamide under reflux conditions, about 3 to 7 hours is required for the reaction completion.

d) (S)-N-[[3-[3-Fluoro-4-[4-morpholinyl]phenyl]-2-oxo-5-oxazolidinyl]methyl]phthalimide produced as above is reacted with hydrazine hydrate or aqueous methyl amine to produce S-N-[[3-[3-Fluoro-4-[4-morpholinyl]phenyl]-2- oxo-5-oxazolidinyl]methyl]amine (Formula I, R₁=R₃ is H; X is O; one R₂ is H and the other R₂ is F; and n is 1). These methods of deprotection are known and described for example in U.S. Pat. No. 5,688,792.

e) S-N-[[3-[3-Fluoro-4-[4-morpholinyl]phenyl]-2-oxo-5-oxazolidinyl]methyl]amine is reacted with acetic anhydride to produce linezolid.

The following examples are given for the purpose of illustrating the present invention and should not be considered as limitations on the scope and spirit of the invention.

EXAMPLES

Example 1

3-Fluoro-4-morpholinyl aniline (39 g) is mixed with R-epichlorohydrin (18.5 g), isopropyl alcohol (200 ml) is added and heated for 16 hours at reflux temperature. The solvent is distilled to give 57 gm of N-[3-Chloro-2-(R)-hydroxypropyl]-3-fluoro-4-morpholinyl aniline.

Example 2

N-[3-Chloro-2-(R)-hydroxypropyl]-3-fluoro-4-morpholinyl aniline (57 g) is dissolved in methylene dichloride (600 ml), diimidazolyl carbonyl (32 g) is added at ambient temperature and the reaction mixture is stirred for 20 hours. Then washed with water and distilled methylene dichloride to give 48 gm of (5R)-5-(chloromethyl)-3-[3-fluoro-4-(4-morpholinyl)phenyl]-2-oxazolidinone.

Example 3

The mixture of (5R)-5-(chloromethyl)-3-[3-fluoro-4-(4-morpholinyl)phenyl]-2-oxazolidinone (60 g), potassium phthalimide (40 g) and Dimethyl formamide (400 ml) is heated for 5 hours at reflux temperature. The reaction mixture is cooled to ambient temperature, poured in to 2 L water and filtered the solid to give 50 gm (S)-N-[[3-[3-Fluoro-4-[4-morpholinyl]phenyl]-2-oxo-5-oxazolidinyl]methyl]phthalimide.

Example 4

Methanol (240 ml) and Hydrazine hydrate (26 g) are added to a flask containing the (S)-N-[[3-[3-Fluoro-4-[4-morpholinyl]phenyl]-2-oxo-5-oxazolidinyl]methyl]phthalimide (40 g), heated for 1 hour at reflux temperature and cooled to room temperature. Then water (500 ml) is added to the reaction mass and extracted with methylene dichloride (300 ml). The combined extractions were washed with water (100 ml) and the solvent distilled to give 20 gm of S-N-[[3-[3-Fluoro-4-[4-morpholinyl]phenyl]-2-oxo-5-oxazolidinyl]methyl]amine.

Example 5

S-N-[[3-[3-Fluoro4-[4-morpholinyl]phenyl]-2-oxo-5-oxazolidinyl]methyl]amine (20 gm) is dissolved in Ethyl acetate (200 ml), Acetic anhydride (20 gm) is added drop wise at ambient temperature and stirred for 1 hour. The reaction mixture is then cooled to 0-5° C., filtered the solid and re-crystallized from Isopropyl alcohol (400 ml) to give 16 gm of N-[[(5S)-3-[3-fluoro-4-(4-morpholinyl)phenyl]-2-oxo-5-oxazolidinyl]methyl]acetamide.

We claimed:

1. A process for the preparation of 5-aminomethyl substituted oxazolidinones of formula I:

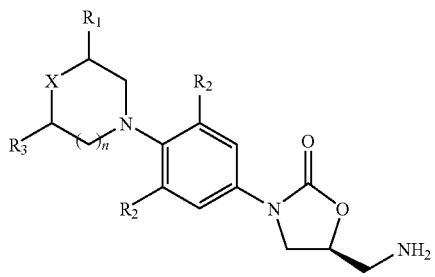

wherein
X is O, S, SO or SO₂;
R₁ is H, CH₃ or CN;
R₂ is independently H, F or Cl;
R₃ is H or CH₃;
n is 0, 1 or 2;
which comprises:
converting the chlorine atom of the chloromethyl oxazolidinone compound of formula V:

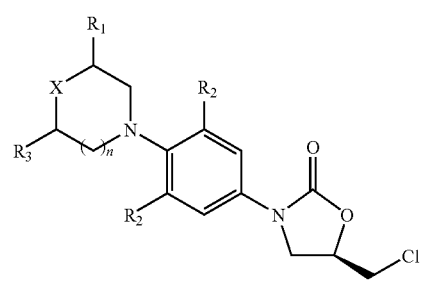

wherein
X is O, S, SO or SO₂;
R₁ is H, CH₃ or CN;
R₂ is independently H, F or Cl;
R₃ is H or CH₃;
n is 0, 1 or 2;
to azide using an azide source selected from the group consisting of sodium azide and potassium azide to prepare an azide compound of formula VI:

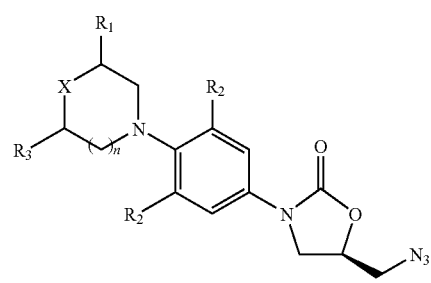

wherein R1, R3, X, R2 and n are as defined in formula I; and hydrogenating the azide compound using a palladium/carbon catalyst to provide the compounds of formula I.

2. The process as defined in claim 1, wherein $R_1=R_3$ is H; $R_2$ is independently H and F; X is O or S; and n is 1.

3. The process as defined in claim 2, wherein $R_1=R_3$ is H; one $R_2$ is H and the other $R_2$ is F; X is O; and n is 1.

4. A process for the preparation of 5-aminomethyl substituted oxazolidinones of formula I:

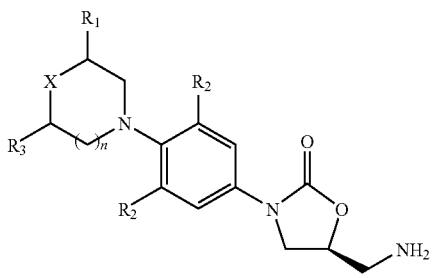

wherein
X is O, S, SO or $SO_2$;
$R_1$ is H, $CH_3$ or CN;
$R_2$ is independently H, F or Cl;
$R_3$ is H or $CH_3$;
n is 0, 1 or 2;
which comprises:
converting the chlorine atom of the chloromethyl oxazolidinone compound of formula V:

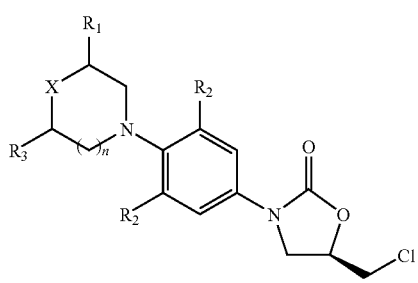

wherein
X is O, S, SO or $SO_2$;
$R_1$ is H, $CH_3$ or CN;
$R_2$ is independently H, F or Cl;
$R_3$ is H or $CH_3$;
n is 0, 1 or 2;
by reacting with potassium phthalimide to provide a phthalimido compound of formula VII:

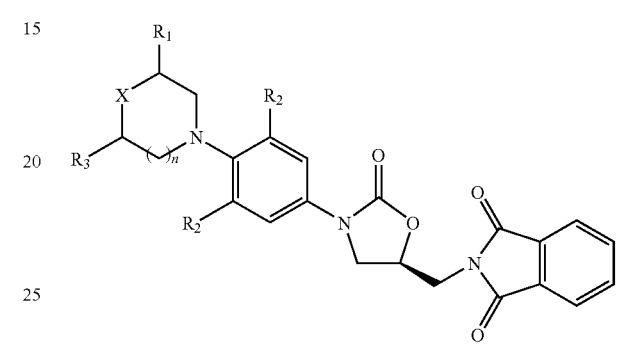

wherein R1, R3, X, R2 and n are as defined in formula I; and
converting the phthalimido compound to the aminomethyl oxazolidinone compounds using either hydrazine hydrate or aqueous methylamine to yield the compounds of formula I.

5. The process as defined in claim 4, wherein $R_1=R_3$ is H; $R_2$ is independently H and F; X is O or S; and n is 1.

6. The process as defined in claim 5, wherein $R_1=R_3$ is H; one $R_2$ is H and the other $R_2$ is F; X is O; and n is 1.

* * * * *